US 6,616,683 B1

(12) United States Patent
Toth et al.

(10) Patent No.: US 6,616,683 B1
(45) Date of Patent: Sep. 9, 2003

(54) METHOD OF MAKING MINIATURIZED SURGICAL FORCEPS

(75) Inventors: Cynthia A. Toth, Durham, NC (US); Ronald F. Overaker, Durham, NC (US); Brian C. Dodge, Durham, NC (US); Brooks W. McCuen, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/563,420

(22) Filed: May 2, 2000

(51) Int. Cl.$^7$ ................................................. B21K 5/00
(52) U.S. Cl. ..................... 606/207; 606/205; 606/206; 606/210; 76/119
(58) Field of Search ..................... 606/205, 206, 606/207, 210, 107; 76/119; 72/367.1, 370.1, 370.11

(56) References Cited

U.S. PATENT DOCUMENTS

| 2,764,905 A | 10/1956 | Thoms |
| 3,589,369 A | 6/1971 | Alksnis |
| 4,253,224 A * | 3/1981 | Hickman et al. .......... 29/157 T |
| 4,258,716 A | 3/1981 | Sutherland |
| 4,427,014 A * | 1/1984 | Bel et al. |
| 4,460,211 A | 7/1984 | Pomeroy |
| 4,634,165 A | 1/1987 | Russell et al. |
| 4,761,028 A | 8/1988 | Dulebohn |
| 4,825,864 A | 5/1989 | Hariri |
| 5,156,609 A | 10/1992 | Nakao et al. |
| 5,222,972 A | 6/1993 | Hill et al. |
| 5,263,958 A | 11/1993 | deGuillebon et al. |
| 5,275,607 A | 1/1994 | Lo et al. |
| 5,370,658 A | 12/1994 | Scheller et al. |
| 5,538,008 A * | 7/1996 | Crowe .......................... 606/170 |
| 5,634,918 A | 6/1997 | Richards |
| 5,653,753 A | 8/1997 | Brady et al. |
| 5,702,402 A | 12/1997 | Brady |
| 5,843,121 A | 12/1998 | Yoon |
| 5,913,874 A | 6/1999 | Berns et al. |
| 6,099,550 A * | 8/2000 | Yoon ........................... 606/205 |
| 6,391,046 B1 | 5/2002 | Overaker et al. |

OTHER PUBLICATIONS

Andrwas E. Guber, Microengineering Processes for Medical Technology, Medical Device Link, www.devicelink.com/mddi/archive/99/11/005.html (1999).

* cited by examiner

Primary Examiner—Michael H. Thaler
(74) Attorney, Agent, or Firm—Nixon & Vanderhye P.C.

(57) ABSTRACT

Miniature surgical forceps are formed from a one-piece tubular member by opposed longitudinal channels machined in a distal end thereof so as to establish a radially opposed pair of unitary forceps jaws. Most preferably, the opposed channels are formed in the distal end of the rigid tubular member by means of electron discharge machining (EDM) techniques. The resulting opposed cross-sectionally arcuate jaw sections may be bent and/or further shaped to achieve the desired final jaw configuration. The inner surfaces of the forceps jaws thereby established may have a filler material deposited in such a manner so as to change the overall shape and/or geometric configuration of the jaws and thereby engineer them to a specific surgical purpose.

21 Claims, 4 Drawing Sheets

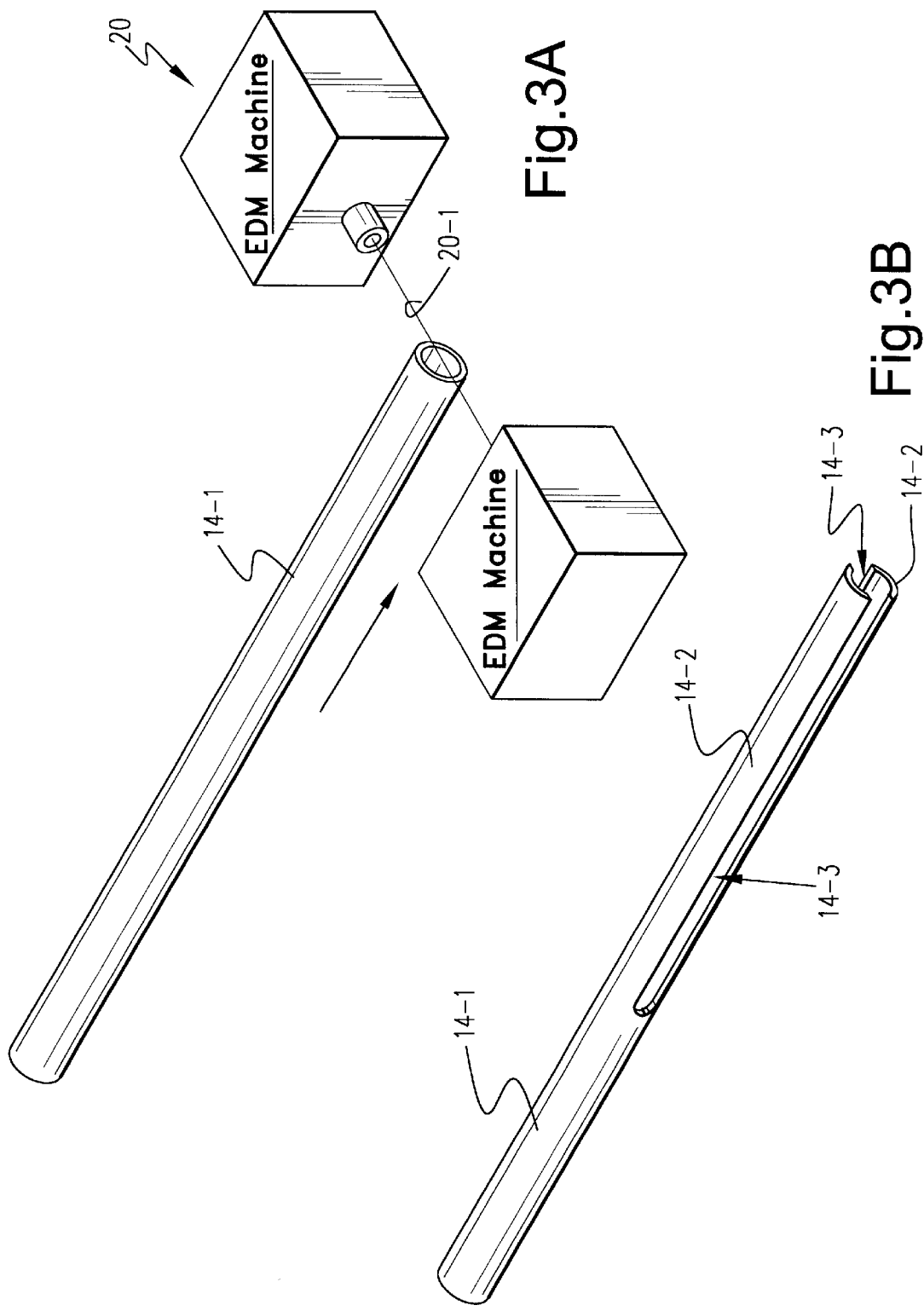

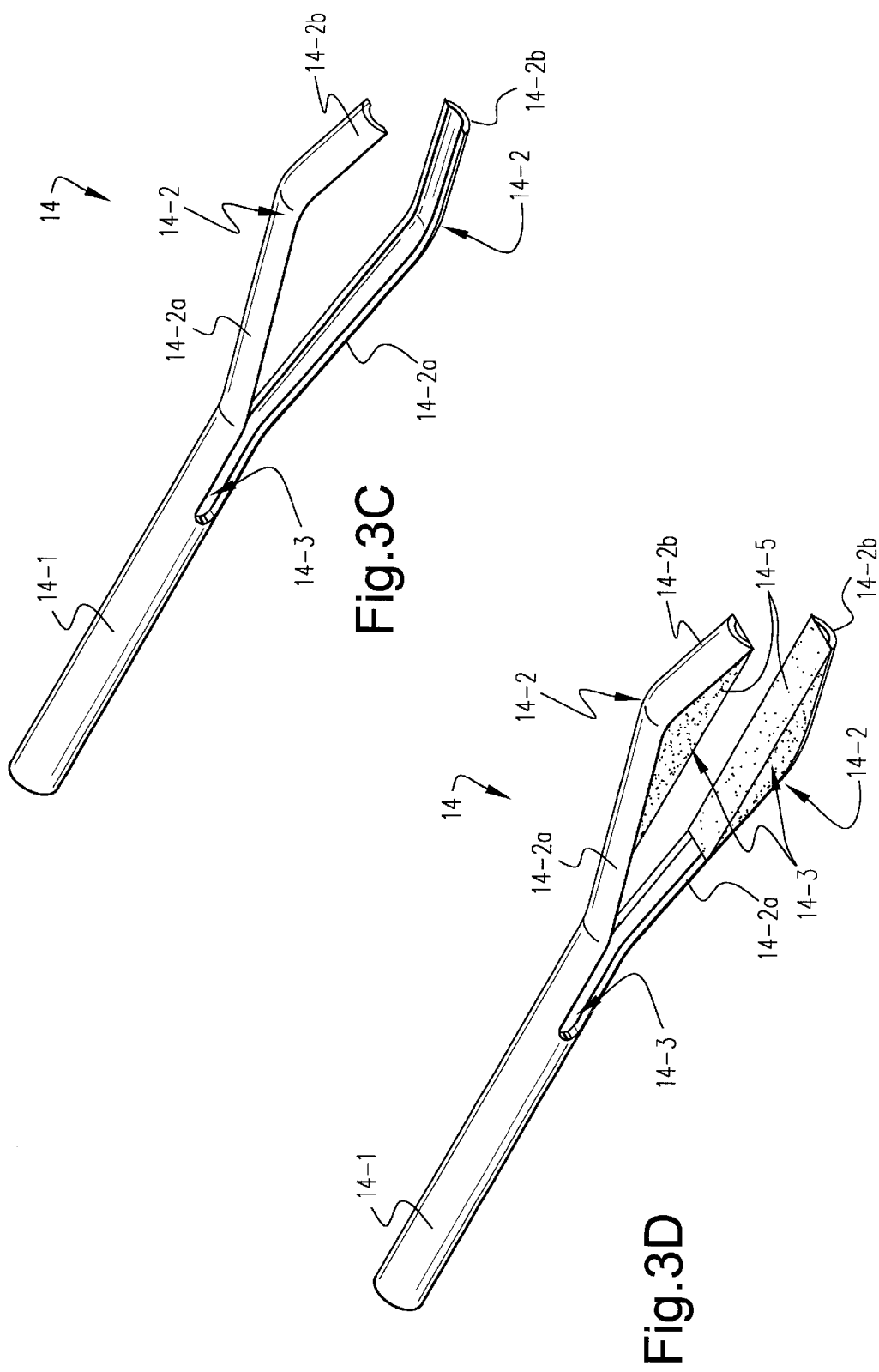

METHOD OF MAKING MINIATURIZED SURGICAL FORCEPS

FIELD OF THE INVENTION

The present invention relates generally to the field of surgical instruments, particularly instruments employed in ophthalmologic surgical procedures, In preferred forms, the present invention relates to miniaturized surgical forceps which are especially well suited for ophthalmologic surgical procedures, for example.

BACKGROUND AND SUMMARY OF THE INVENTION

During intraocular surgery, instruments are positioned within the anterior chamber or vitreous cavity through microscopic incisions through the eye wall. Each placement and removal of an instrument can cause damage to adjacent structures (such as retinal tear with detachment or tear of Descemet's membrane). A goal, therefore, is to limit the number of times instruments are introduced and replaced within the eye during intraocular surgery.

It would therefore be highly desirable if a surgical instrument, especially forceps, could be provided which are particularly well suited for use during intraocular surgery that had a hollow lumen. Such an instrument would therefore allow for the delivery of materials and/or secondary instruments in concert with the forceps action and thereby decrease the need for repeated withdrawal and reinsertion of instruments and material delivery devices. For example, the actions that could be performed with such an instrument include, the infusion of intraocular liquid or gas; injection of specific fluids such as a dye or a perfluorocarbon liquid; manipulation with small picks, hooks, aspirating cannula or blunt probe, optical diagnostics and imaging by means of video fiber or other optical diagnostic fiber; cutting with a fine scalpel or laser fiber; and/or delivery of light or laser energy.

Broadly, the present invention is embodied in miniature surgical forceps formed from a lumen-defining tubular member. The hollow lumen of the miniature surgical forceps of the present invention thereby permit the actions noted immediately above to be performed in simultaneously in concert with the forceps action. That is, the safe delivery of additional instrumentation to the surgical site can be performed in concert with the actions of the microforceps tip without removing instruments through the eye wall. Thus, the forceps of the present invention have greatly improved and enhanced utility since additional instrumentation may be utilized to work with or aid in positioning of tissues with the grasp of the forceps.

According to preferred embodiments, the miniature surgical forceps of the present invention are provided with opposed longitudinal channels machined in a distal end of a tubular member so as to establish an opposed pair of forceps jaws. Most preferably, the opposed channels are formed in the distal end of the rigid tubular member by means of electrical discharge machining (EDM) techniques. Thus, according to the present invention, opposed radial channels are formed in a lengthwise extent of the distal end of a rigid tubular member by EDM techniques. The resulting opposed cross-sectionally arcuate jaw sections may be bent and/or further shaped to achieve the desired final jaw configuration.

The inner surfaces of the forceps jaws thereby established may be provided with a suitable filler material so as to establish a desired forceps surface. For example, the filler material may be a hardened material (e.g., a tungsten carbide, electroless nickel or like hardened materials) to provide structural reinforcement to the forceps jaws or may be a compliant material, such as an elastomeric (e.g., silicone rubber) type material. These materials may thus be deposited onto the forceps jaws in a manner which changes the overall shape and/or geometric configuration of the jaws and thereby engineer them to a specific surgical purpose. In addition, the filler material may be coated with a desired abrasive material (e.g., fine powders of diamond dust, aluminum oxide, tungsten carbide and the like) so as to increase the forceps jaws' coefficient of friction.

These and other aspects and advantages of the present invention will become more clear from the following detailed description of the preferred exemplary embodiments thereof.

BRIEF DESCRIPTION OF THE ACCOMPANYING DRAWINGS

Reference will hereinafter be made to the accompanying drawings, wherein like reference numerals throughout the various FIGURES denote like structural elements, and wherein, FIG. 1 is a side elevation view showing one exemplary embodiment of a miniaturized surgical forceps according to the present invention;

FIGS. 3A–3D is a schematic perspective views showing the manner in which the surgical forceps of this invention is made;

DETAILED DESCRIPTION OF THE INVENTION

Figure 1:
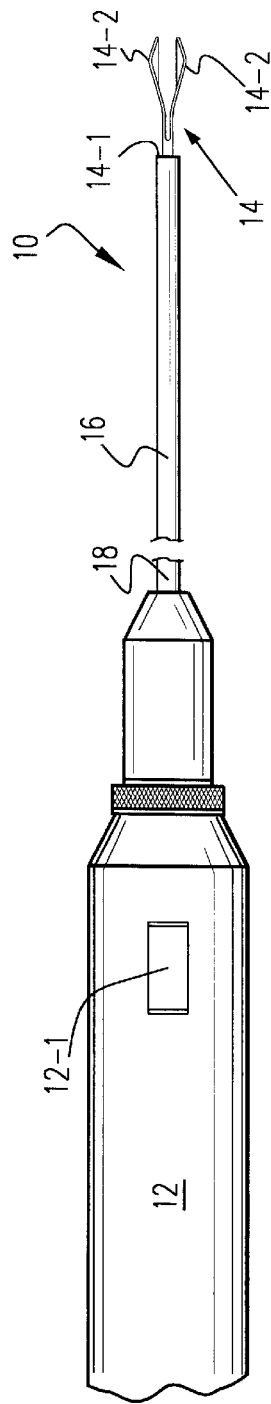

Accompanying FIG. 1 shows one preferred embodiment of a surgical instrument 10 according to the present invention. In this regard, the instrument 10 includes a proximal handle section 12, a distal forceps section 14 and an intermediate tubular support section 16. The intermediate tubular support section 16 may itself be sleeved within a proximal reinforcement tube 18 as may be desired for purposes of imparting structural integrity to the instrument 10.

The handle section 12 is, in and of itself, highly conventional. For example, the handle section 12 may be conventional Sutherland-type handles of the variety disclosed in U.S. Pat. No. 5,634,918 (the entire content of which is incorporated hereinto fully by reference) or the omniactuatable hand-held device disclosed in U.S. Pat. No. 6,391,046 B1 (the entire content of which is expressly incorporated hereinto by reference). The handle section 12 may also be motor-actuated, if desired.

The handle section 12 is coupled operatively to the proximally extending stem 14-1 of the forceps section 14. By manipulating the handle section's actuator (which is shown schematically by reference numeral 12-1 in FIG. 1), the stem 14-1 can be caused to retract rearwardly within the intermediate tubular section 16 with which it is coaxially sleeved. Retraction of the forceps stem 14-1 will, in turn, cause the opposed jaws 14-2 to be forcibly moved toward one another against their inherent resilient forces. Alternatively or additionally, the actuator 12-1 may be coupled to one end of wires (not shown) whose other end is attached to a respective one of the jaws 14-2. Movement of the button 12-1 will thereby cause the jaws 14-2 to move towards and away from one another as may be desired.

Figure 2:
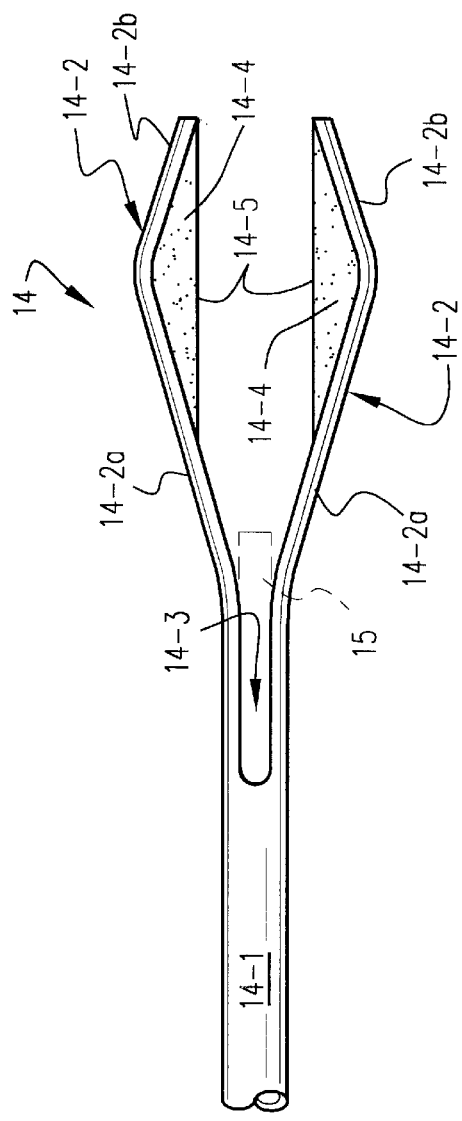
FIG. 2 is an enlarged elevational view of the tip employed in the surgical forceps of FIG. 1.

Accompanying FIG. 2 perhaps shows the distal forceps section 14 in greater clarity. As shown, the opposed forceps jaws 14-2 are established by a longitudinally extending channel 14-3 formed in a distalmost section of the tubular forceps stem 14-1. Each of the forceps jaws 14-2 is therefore the cross-sectionally arcuate, unitary (i.e., one-piece) remnant of the distalmost section of the tubular forceps stem 14-1. These remnants have thus been further fashioned by a proximal outwardly bent section 14-2a and an immediately distal inwardly bent section 14-2b. The jaws 14-2 thereby fashioned are generally V-shaped which provides a seat for a suitable filler material 14-4 which thereby forms the opposed gripping surfaces 14-5 of the forceps jaws 14-2.

The filler material 14-4 may be a hardened material (e.g., a tungsten carbide, electroless nickel or like hardened materials) to provide structural reinforcement to the forceps jaws 14-2 or may be a compliant material, such as an elastomeric (e.g., silicone rubber) type material. These materials may thus be deposited onto the forceps jaws in a manner which changes the overall shape and/or geometric configuration of the jaws and thereby engineer them to a specific surgical purpose. In addition, the filler material 14-4 may be coated with a desired abrasive material (e.g., fine powders of diamond dust, aluminum oxide, tungsten carbide and the like) so as to increase the forceps jaws' coefficient of friction.

As noted above, the lumen defined by the longitudinally extending channel 14-3 of the tubular forceps stem 14-1 provides a convenient means by which an elongate element (shown schematically by dashed line in FIG. 2 as reference numeral 15) may be employed by the attending surgeon. The elongate element 15 may be any of a variety of devices that may be needed by the attending surgeon for use in concert with the forceps. Thus, the element 15 may be tubular so as to allow the infusion of intraocular liquid or gas, injection of specific fluids such as a dye or a perfluorocarbon liquid or the like. The distal end of the element 15 may be in the form of a miniature pick, hooks, aspirating cannula, blunt probe, scalpel or the like that may be needed by the surgeon. Alternatively, the element 15 may be an optical fiber to allow optical diagnostics and imaging to be accomplished and/or for the delivery of laser light energy as may be needed.

Accompanying FIGS. 3A–3D schematically depict a presently preferred technique for forming the miniature forceps 10 of this invention. As shown in FIG. 3A, the distal end of a length of tubing (e.g., a section of a conventional 19 ga. or smaller stainless steel tubular needle) forming the stem 14-1 is axially translated relative to an EDM wire 20-1 provided as a component part of a conventional EDM system 20. When energized, the EDM wire 20-1 thereby removes material from the distal end of the stem 14-1 forming radially opposed, longitudinally extending channels 14-3 thereby establishing the opposed pair of forceps jaws 14-2 as shown in FIG. 3B. It will be observed that the jaws in FIG. 3B have not been further fashioned by bending, but instead are depicted in a state immediately following the machining by the EDM system. However, in FIG. 3C, each of the cross-sectionally arcuate jaws 14-2 have been further fashioned by bending so as to form the proximal outwardly bent section 14-2a and the immediately distal inwardly bent section 14-2b. It will be seen in FIG. 3C that the section 14-2a is bent outwardly at a location which is distal to the proximal extent of channels 14-3. The generally V-shaped jaws 14-2 thereby fashioned may then receive a suitable hardened material (e.g., a tungsten carbide, electroless nickel or like hardened materials) which thereby forms the opposed gripping surfaces 14-4 of the forceps jaws 14-2 as shown in FIG. 3D.

It will be understood, that the lumen of the stem 14-1 is open to the space defined between the jaws 14-2. Such a structural attribute of the forceps instrument 10 of this invention can be quite advantageous during certain surgical procedures. Thus, for example, the instrument may be connected to a aspiration source providing suction through the lumen of the stem 14-1 which may assist the surgeon to more easily grasp desired tissue. Alternatively, the lumen of the stem 14-1 may be connected to a source of irrigation fluid to allow the surgeon to irrigate the surgical field simultaneously while operating the miniature forceps jaws 14-2 of the instrument 10.

Figure 4:
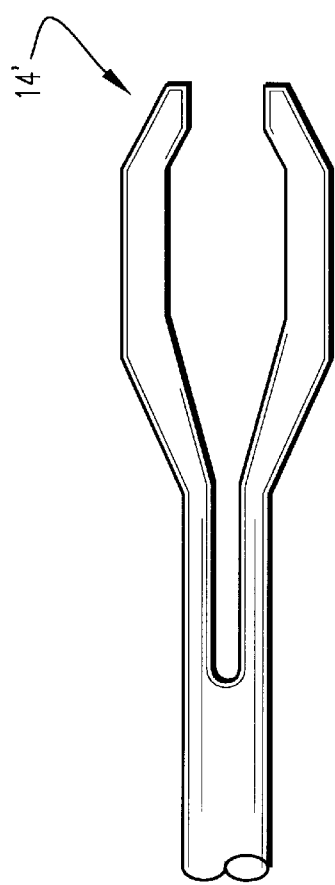
FIGS. 4–6 are each enlarged elevational views depicting other possible tip embodiments for the surgical forceps of the present invention.
Figure 5:
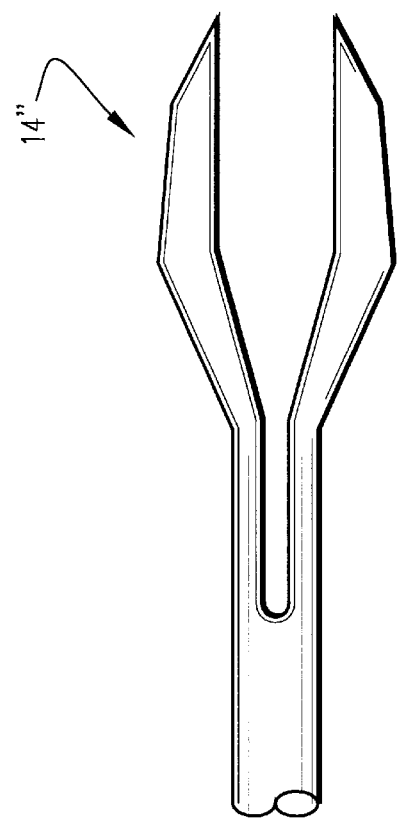
Figure 6:
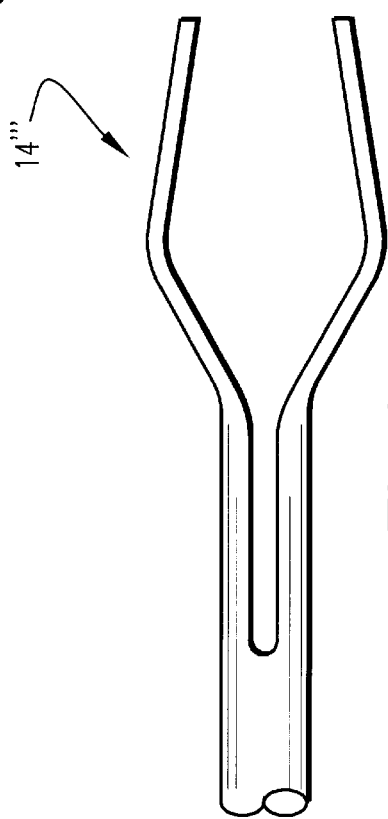

The forceps jaws 14-2 may be fashioned as desired so as to achieve a wide variety of jaw designs suitable for specific surgical purposes. For example, the forceps jaws 14-2' shown in FIG. 4 may be provided with multiple bends and machined so as to exhibit a relatively blunt tip, while the forceps jaws 14-2" may be machined to exhibit a relatively sharp tip. And, as shown in FIG. 6, the filler material may be omitted from the forceps jaws 14-2'''.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of making miniature surgical forceps comprising providing a 19 gauge or smaller rigid tubular member, and removing material from longitudinal regions of a distal end of said tubular member so as to form respective longitudinally extending channels therein which thereby define an opposed pair of forceps jaws from respective remnants of said distal end of said tubular member.

2. The method of claim 1, wherein said material is removed from radially opposed longitudinal regions of said distal end of said rigid tubula member so as to form a respective pair of radially opposed longitudinally extending channels therein.

3. The method of claim 1 or 2, further comprising depositing a filler material onto said respective remnants.

4. The method of claim 3, wherein said filler material is deposited onto an interior of each of said respective remnants.

5. The method of claim 4, wherein said filler material is selected from hardened or compliant materials.

6. The method of claim 3, further comprising an abrasive coating on at least a surface portion of said filler material.

7. The method of claim 1 or 2, further comprising bending said remaining remnants into a generally V-shaped configuration.

8. The method of claim 7, further comprising depositing a filler material onto said V-shaped configuration of said respective remnants.

9. The method of claim 8, wherein said filler material is deposited onto an interior of each of said respective remnants.

10. The method of claim 1 or 2, wherein said material is removed using electrical discharge machining.

11. A method of making miniature forceps comprising forming a radially opposed pair of proximally extending longitudinal channels in a distalmost end of a 19 gauge or smaller rigid tubular member to thereby establish an opposed pair of forceps jaws thereat, wherein said channels are formed by removing material from said distalmost end of said rigid tubular member.

12. The method of claim 11, wherein said material is removed by electrical discharge machining.

13. The method of claim 11, further comprising depositing a filler material onto said respective jaws.

14. The method of claim 13 wherein said filler material is deposited onto an interior of each of said jaws.

15. The method of claim 11, further comprising bending said jaws into a generally V-shaped configuration.

16. The method of claim 15, further comprising depositing a filler material onto said V-shaped configuration of said jaws.

17. The method of claim 16, wherein said filler material is deposited onto an interior of each of said respective jaws.

18. A method of making miniature surgical forceps comprising the steps of:

(i) providing a 19 gauge or smaller rigid tubular member;

(ii) effecting relative axial translation between a distal end of the tubular member and an energized wire associated with an electron discharge machining (EDM) system so as to remove material from said distal end of the tubular member so as to form a pair of radially opposed, longitudinally extending channels which thereby establish an opposed pair of cross-sectionally arcuate remnant sections at said distal end; and thereafter (iii) outwardly bending said remnant sections to establish an opposed pair of forceps jaws.

19. The method of claim 18, wherein step (iii) is practiced by bending said remnant sections at a location distally of a proximal extent of said channels.

20. The method of claim 19, wherein step (iii) is practiced by bending a proximal outwardly bent section and an immediately distal inwardly bent section so as to form a pair of opposed generally V-shaped forceps jaws.

21. The method of claim 20, which comprises depositing a filler material into said cross-sectionally arcuate remnants.

* * * * *